(12) United States Patent
Smolyaninov et al.

(10) Patent No.: US 7,943,908 B2
(45) Date of Patent: May 17, 2011

(54) SENSOR SYSTEM WITH SURFACE-PLASMON-POLARITON (SPP) ENHANCED SELECTIVE FLUORESCENCE EXCITATION AND METHOD

(75) Inventors: Igor I. Smolyaninov, Columbia, MD (US); Yu-Ju Hung, Fremont, CA (US); Christopher C. Davis, Bowie, MD (US)

(73) Assignee: University of Maryland, College Park, MD (US)

( * ) Notice: Subject to any disclaimer, the term of this patent is extended or adjusted under 35 U.S.C. 154(b) by 0 days.

(21) Appl. No.: 12/017,575

(22) Filed: Jan. 22, 2008

(65) Prior Publication Data

US 2009/0045351 A1    Feb. 19, 2009

Related U.S. Application Data

(60) Provisional application No. 60/885,996, filed on Jan. 22, 2007.

(51) Int. Cl.
*G01J 1/58* (2006.01)
(52) U.S. Cl. .................................. 250/458.1
(58) Field of Classification Search ............ 250/458.1
See application file for complete search history.

(56) References Cited

U.S. PATENT DOCUMENTS

| | | | |
|---|---|---|---|
| 5,006,716 A * | 4/1991 | Hall ........................... 250/458.1 |
| 5,442,448 A | 8/1995 | Knoll |
| 5,907,408 A | 5/1999 | Naya et al. |
| 5,994,150 A * | 11/1999 | Challener et al. ............ 436/518 |
| 6,078,705 A * | 6/2000 | Neuschafer et al. ............ 385/12 |
| 6,317,206 B1 | 11/2001 | Wulf |
| 6,707,561 B1 | 3/2004 | Budach et al. |
| 6,771,376 B2 | 8/2004 | Budach et al. |
| 6,782,179 B2 | 8/2004 | Bozhevolnyi et al. |
| 6,831,748 B2 | 12/2004 | Tittel et al. |
| 6,867,869 B2 | 3/2005 | Budach et al. |
| 6,870,630 B2 | 3/2005 | Budach et al. |
| 7,064,844 B2 | 6/2006 | Budach et al. |
| 7,102,752 B2 | 9/2006 | Kaylor et al. |
| 7,397,043 B2 | 7/2008 | Ja |
| 2005/0053974 A1 | 3/2005 | Lakowicz et al. |
| 2005/0079635 A1 * | 4/2005 | Norman ........................ 436/514 |
| 2006/0216204 A1 | 9/2006 | Budach et al. |
| 2006/0238767 A1 | 10/2006 | Chen et al. |
| 2007/0164377 A1 * | 7/2007 | Gruhlke et al. ............... 257/414 |

OTHER PUBLICATIONS

Sullivan et al. Directional, enhanced fluorescence from molecules near a periodic surface, Applied Optics vol. 33, No. 13 (May 1, 1994), pp. 2447-2454.*

Hung, et al., "Fluorescence enhancement by surface gratings", Optics Express, vol. 14, Issue 22, Oct. 30, 2006, pp. 10825-10830.

* cited by examiner

*Primary Examiner* — David P Porta
*Assistant Examiner* — Shun Lee
(74) *Attorney, Agent, or Firm* — Rosenberg, Klein & Lee

(57) ABSTRACT

In a sensor system, an active sensor chip includes an array of periodically-patterned dielectric active sensor patches of different periodicities and geometries formed on a metal film. A specimen under study is positioned on each patch, and the active sensor chip is interrogated by illumination the patches in a predetermined sequence to result in a fluorescence response from each patch enhanced by SPP. The intensity of the fluorescence response is controlled by varying the wavelength, incidence angle, azimuthal orientation and polarization direction of the excitation light beam as the function of the periodicity of the illuminated patch. The system is compatible with commercial fluorescence microscopes and scanned laser interrogation systems.

27 Claims, 10 Drawing Sheets

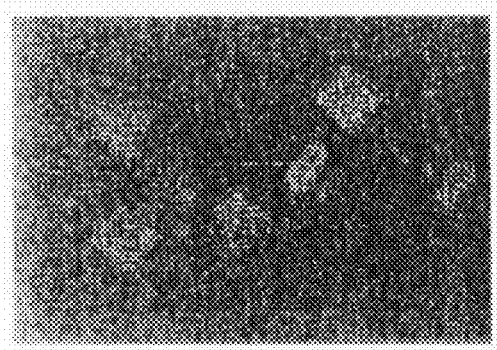
FIG.12A  FIG.12B
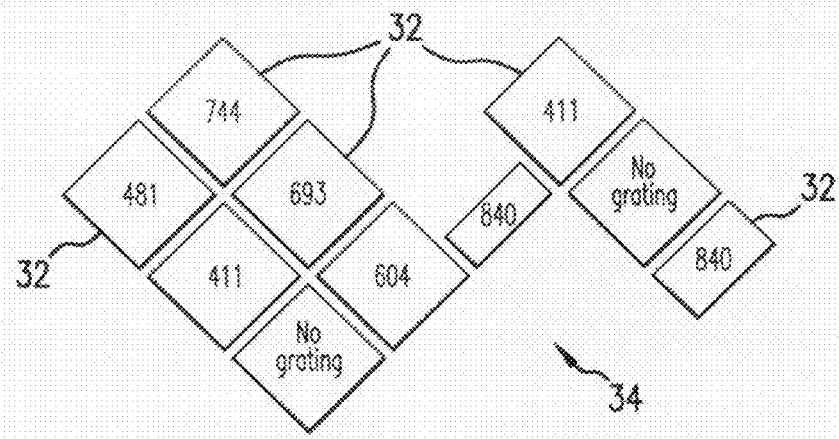
FIG.12C

SENSOR SYSTEM WITH SURFACE-PLASMON-POLARITON (SPP) ENHANCED SELECTIVE FLUORESCENCE EXCITATION AND METHOD

STATEMENT REGARDING FEDERALLY SPONSORED RESEARCH

The invention described herein was developed through research sponsored by the NSF, Contract Nos. ECS0304046 and ECE0508275. The United States Government has certain rights to the invention.

RELATED APPLICATION DATA

This Utility patent application is based on Provisional Patent Application Ser. No. 60/885,996 filed on 22 Jan. 2007.

FIELD OF THE INVENTION

The invention described herein is related to fluorescence detection, and particularly, to a Surface-Plasmon-Polariton (SPP) enhanced fluorescence sensor.

More in particular, the present invention is directed to a sensor system based on Surface-Plasmon-Polariton assisted fluorescence excitation attained by forming a periodically patterned dielectric nano-structured surface on a metal film which facilitates controlling the behavior of the surface plasmon polaritons existing in the vicinity of the boundary between the metal and the dielectric to obtain an enhanced fluorescence signal where the strength of the signal is controlled by selecting control parameters optimal for the periodicity and geometry of the dielectric nano-structured surface.

In overall concept, the present invention is directed to a sensing system applicable to the analysis of biological, chemical, etc. specimens, and in which an array of periodically patterned dielectric patches of various periodicities and geometries are positioned on a conductive film to form a multi-patch sensor chip for analysis of a plurality of specimens of interest by interrogating the patches under the optical excitation conditions controlled to obtain a strong fluorescent response from each specimen.

BACKGROUND OF THE INVENTION

Fluorescent molecules are widely used in numerous research and sensing applications. The scientific community in the field of the fluorescence detection is particularly interested in an understanding of how fluorescent molecules behave in various experimental geometries, especially in close proximity to metal and dielectric interfaces. In various previous studies, the radiation patterns of fluorescent molecules deposited on dielectric/dielectric or dielectric/metal interfaces have been calculated and observed. However, further development of the most efficient geometries for fluorescence detection is still needed.

Most previous Surface-Plasmon Resonance (SPR) sensors, excite the surface plasmons in a total internal reflection geometry. This is shown in Lakowicz, et al., U.S. Patent Application Publication 2005/0053974, where a sensing metal film is positioned on a high refractive index medium (glass), and the excitation light enters into the system for interaction with a metal film at an angle θ through the glass medium. In this arrangement, when a surface plasmon is excited, a significant enhancement of the optical field associated with the surface plasmon results. This evanescent field extends away from the metal film by about one wavelength of the illumination light beam into the air region next to the metal film. To fluoresce effectively, the fluorescent molecules must be oriented correctly and be localized in the vicinity of the metal film.

In the Lakowicz, et al. arrangement, the fluorescence response occurs at a very well defined beam incidence angle to the film, and the fluorescence signal passes to a detector through the glass. The drawback of Lakowicz, et al.'s system is that the fluorescence emerges as a cone of light on the backside of the optical arrangement making the detection geometry difficult and inflexible. The total internal reflection geometry used by Lakowicz, et al. and in various prior art sensors, makes them difficult to use in conventional fluorescence detection since the fluorescence does not emerge from the air (front) side of the device and further requires complex optics.

It would be desirable therefore to eliminate the deficiencies of the prior art fluorescence sensors by devising a fluorescence sensor compatible with commercial Fluorescence Optical Microscopes (FOMs).

SUMMARY OF THE INVENTION

It is therefore an object of the present invention to provide a sensor system with Surface-Plasmon-Polariton enhanced selected fluorescence excitation which is compatible with the geometry of current commercial Fluorescent Optical Microscopes (FOM) by allowing the illumination and detection from the front (air) side of the sample.

It is a further object of the present invention to provide a sensor system based on Surface-Plasmon-Polariton enhanced selected fluorescence excitation in which the behavior of the surface plasmon polaritons is controlled in an elegant and efficient fashion to obtain a strong fluorescent response.

It is another object of the present invention to provide a sensor system fully applicable in genomic, proteomic, chemical and biological applications which permits a sufficiently precise determination of presence of fluorescent genes, cells, DNA oligonucleotides, c-DNA, RNA, antibodies, antigens, proteins, etc., referred to herein further as fluorescent target molecules (particles) in specimens under study.

It is still an object of the present invention to provide an active sensor chip formed of a periodically nano-patterned dielectric layer on a conductive film in which fluorescent pattern and the intensity of the fluorescent response are controlled by varying the wavelength of the incident light beam, as well as incidence angles, polarization direction, and azimuthal orientation of the light beam relative to the periodically nano-patterned dielectric layer, and by selecting the surface functionalization parameters adjusted for a periodicity of the periodically patterned dielectric layer.

It is an additional object of the present invention to provide an active sensor chip with specimens applied to a plurality of dielectric periodically nano-patterned sensor patches of different periodicities, and alternatively of distinct geometries, which are interrogated by illuminating the patches in a predetermined sequential order. During the interrogation, the wavelength of the illumination, incidence angle, polarization directions, and azimuthal orientation of the light beam are controlled depending on the periodicity of the respective periodically patterned patch to provide optimal conditions for generation of the fluorescence signal emanating from each patch for precise detection of particulates of interest in each specimen.

The sensor system with Surface-Plasmon-Polariton (SPP) enhanced selective fluorescence excitation comprises an active sensor chip which includes a conductive layer and a dielectric layer deposited on the conductive layer and patterned to form a single or a plurality of active sensor patches each having a periodically patterned surface of a predetermined periodicity and geometry. A specimen under study, which contains fluorescently labeled target particles of interest, is positioned on the periodically patterned surface of the active sensor patch.

An excitation light beam is directed onto the periodically patterned surface of the active sensor patch through the specimen under study, so that target particles of interest generate a fluorescence signal enhanced in a predetermined controlled fashion by excitation of the Surface-Plasmon Polaritons in the vicinity of the boundary formed between the conductive layer and the dielectric periodically patterned active sensor patch.

If a multi-patch sensor chip is used for specific applications in biological and chemical studies, active sensor patches of different periodicities (and alternatively of different geometries) are positioned on the conductive layer in a predetermined array fashion. These sensor patches may be contoured in different configurations, for example, in square, circular, elliptical, rectangular, etc. shapes. In the active sensor patches periodically disposed nano-elements may be shaped, for example, as parallel lines, circles, parabolas, ellipses, in addition they may present arrays of shapes in a matrix arrangement, including holes, bumps, and repeated shapes of different symmetry.

A plurality of specimens under study are positioned on the multi-patch sensor chip, with each specimen on a respective patch. The patches are interrogated in a predetermined sequential fashion with the excitation light beam of a controlled wavelength. The incidence angle of the excitation light beam on each patch, as well as its azimuthal orientation and polarization direction relative to the periodically disposed nano-elements in each patch, are also controlled to control the behavior of the Surface-Plasmon Polaritons (SPP) at the boundary between the patch and the conductive layer to obtain a fluorescence response from the particles of interest in the specimen under study by sufficient intensity.

The periodically disposed nano-elements in each patch are formed as dielectric undulations including walls in a predetermined shape erected from the conductive layer and trenches defined between the walls. The active sensor patch, in a single patch or a multi-patch implementation, may further include conductive films covering top portions of the walls of the periodic nano-structured surface.

Alternatively, the active sensor chip, either in its single patch or multi-patch implementation, may be formed from at least two conductive layers sandwiching a dielectric periodically patterned structure therebetween. This dielectric periodically patterned structure may be formed of a single dielectric, or alternatively of several dielectric materials.

A processor unit controls the interrogation process through a control unit which is operatively coupled to the source of excitation (for example, a laser), and to the active sensor chip for controlling the mode of interrogation and the parameters of the interrogation, such as wavelength of the excitation light beam, incidence and azimuthal angles, as well as polarization direction, of the light beam.

Different fluorescence dyes, including different surface tags, may be used for different patches in a multi-patch sensor chip arrangement. The surface tags bind specifically to fluorescent target particles of interest. The corrugated surface may help to capture more test material thus increasing the concentration of fluorophore labels (fluorescently labeled target particles of interest) on the surface. The periodically patterned surface holds binding agents and/or fluorophores in close proximity to the metal film, which is substantially the place where fluorescence by SPPs is efficiently excited. The trajectories of the SPPs are modified by the periodically shaped nano-structures to produce excitation "hot spots" determining the patterns of excitation. By controlling the behavior of the SPPs, e.g., the trajectories of their propagation, by varying the wavelength, incident angles, polarization direction, azimuthal orientation of the excitation light beam, the fluorescence patterns from surface bound fluorophores (fluorescently labeled target particle of interest) may be controlled to strengthen the fluorescent signal and to discriminate against fluorescence from non-bound fluorophores in a specimen above the surface of the patch.

The illumination of the active sensor chip may be conducted either by scanning the laser beam over the surface of the chip or by rotating and linearly displacing the sensor chip under the localized laser beam.

In another aspect thereof, the present invention provides a method for enhancing selective fluorescence excitation in a sensor system which includes the steps of:
   forming a dielectric periodically patterned patch including periodically disposed nano-elements on a conductive layer;
   functionalizing the periodically patterned dielectric patches with surface tags;
   positioning a specimen under study above the periodically patterned dielectric patch;
   exciting surface plasmon polaritons in the vicinity of a boundary formed between a periodically patterned dielectric patch and the conductive layer by applying thereto an excitation light beam of a predetermined wavelength through the specimen;
   controlling the surface plasmon polariton behavior to enhance the fluorescent response and to obtain a desired fluorescent pattern distinct for each target particle of interest.

The present method further comprises the steps of selecting specific surface tags, the wavelength, an incidence angle and azimuthal angle, as well as polarization direction of the excitation light beam in accordance with the periodicity and geometry of the periodically patterned patch.

In a further aspect of the present invention, the present method for detecting fluorescence in specimens, includes the steps of:
   forming a plurality of periodically patterned dielectric active sensors to create a multi-patch sensor chip on a conductive layer, each of the active sensor patches including a plurality of periodically disposed nano-elements of respective geometry and periodicity,
   functionalizing each periodically patterned dielectric active sensor patch with a respective surface tag,
   positioning a plurality of specimens on the multi-patch sensor chip, each specimen on a respective patch, and
   generating an excitation light beam, and illuminating the periodically patterned dielectric active sensor patches by the excitation light beam through the specimens positioned thereon in a predetermined sequential order to cause generation of a fluorescent response from each specimen assisted by Surface-Plasmon Polaritons excitation in a vicinity of a boundary formed between the conductive layer and the periodically patterned dielectric active sensor patch.

The behavior of the Surface-Plasmon Polaritons is controlled by either changing the wavelength of the excitation light beam, or incidence angle, azimuthal orientation of the excitation light beam relative to the nano-elements on the respective active sensor patch. A database of relationships between the control parameters and periodicity (as well as geometries) of the nano-structured periodically patterned dielectric patches is kept in the memory of the sensor system and inquired by a processor to apply the control parameters through a control unit in the system. The detected fluorescence response is further processed and compared to reference fluorescence patterns to determine the nature of the particles of interest in the specimen.

These and other features and advantages of the present invention will become apparent after reading a further description of the preferred embodiment in conjunction with the patent drawings.

BRIEF DESCRIPTION OF THE DRAWINGS

FIG. 10A illustrates the arrangement of gratings of different periodicities, FIG. 10B is the FOM picture taken under the polarized Hg lamp wherein E-field is parallel to the grating trenches, FIG. 10C is the FOM picture taken under the polarized Hg lamp when the E-field is perpendicular to the grating trenches;

FIGS. 12A-12C represent the results of study of the fluorescence depending on the incidence angle, wherein FIG. 12A is a fluorescence picture taken at the angle $\alpha=30°$, FIG. 12B represents a picture taken at $-2°$ incidence angle, and FIG. 12C is a schematic representation of the pattern arrangement used in FIGS. 12A and 12B;

DESCRIPTION OF THE PREFERRED EMBODIMENT OF THE PRESENT INVENTION

Figure 1:
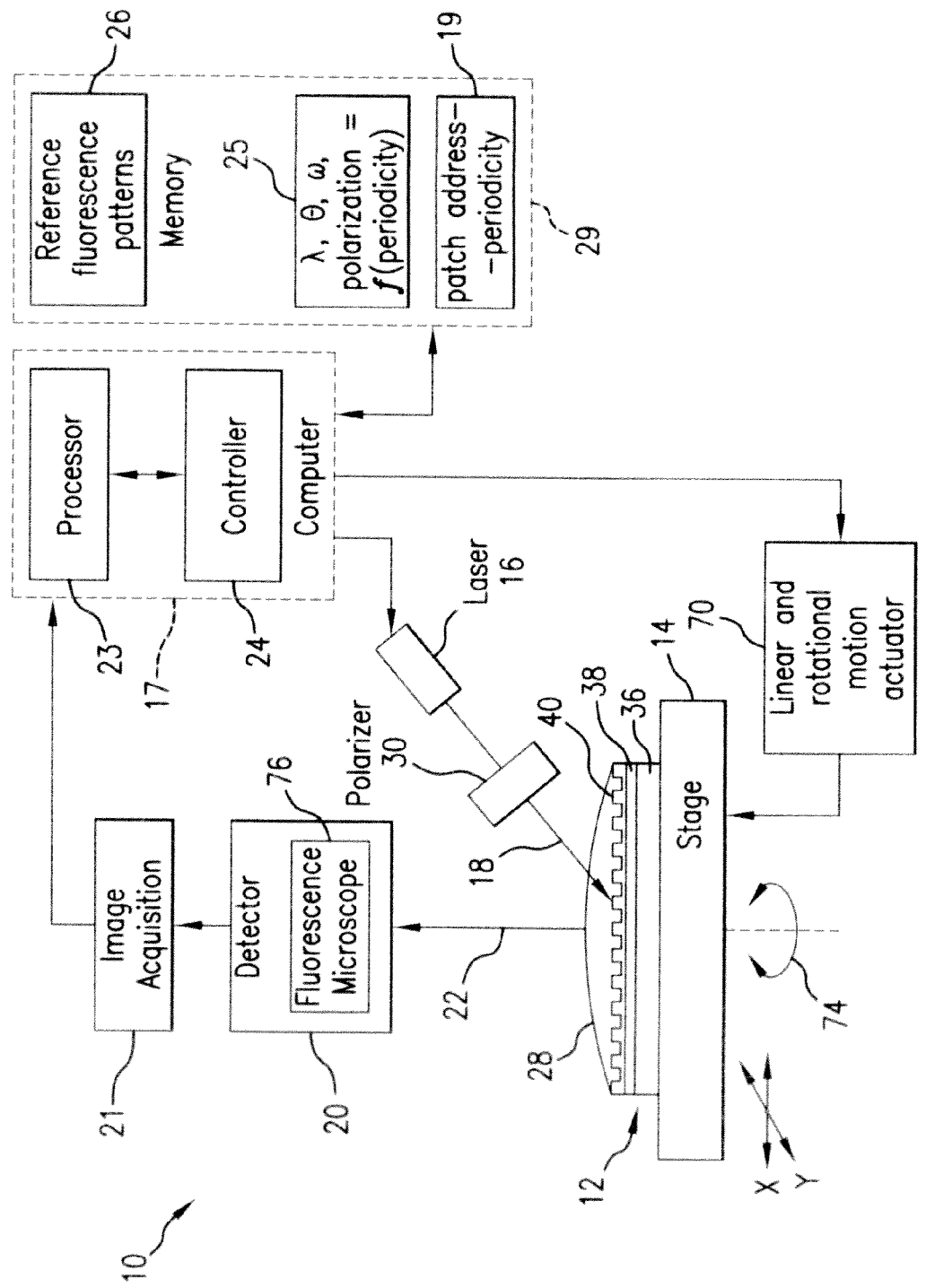
FIG. 1 is a schematic representation of the sensor system of the present invention.

Referring to FIG. 1, a sensor system 10 of the present invention includes an active sensor chip 12 positioned on a stage 14 and secured thereto, a source of excitation light 16 for generating an excitation light beam 18, a computer 17, a detector unit 20 for detecting a fluorescence signal 22, an image acquisition unit 21, a processor unit 23 for processing the detected fluorescence signal and controlling the parameters of sensor system 10, as will be further described in detail. The system 10 further includes a controller unit 24 actuated by the processor unit 23 to apply the control parameters to the excitation source 16 and to the stage 14, as will be presented in detail further herein.

The computer 17 communicates with a database 25 which contains controlling parameters and relationships therebetween to apply the latter to the system 10 during interrogation of the active sensor chip 12, as will be described in further paragraphs. The computer 17, specifically the processor unit 23 therewithin is also configured for comparison of the detected fluorescence signal with the database 26 of the reference fluorescence patterns to identify the nature of the particle of interest which emanates the fluorescence signal 22. Both databases 25, 26 are preferably contained in the memory 29 of the computer 17.

In the sensor system 10, a specimen 28 under study is positioned on the active sensor chip 12.

A polarizer unit 30 may alternatively be positioned at the optical path of the excitation light beam 18 to polarize the same in a predetermined direction for the purposes as will be described in detail in further paragraphs.

Figure 4:
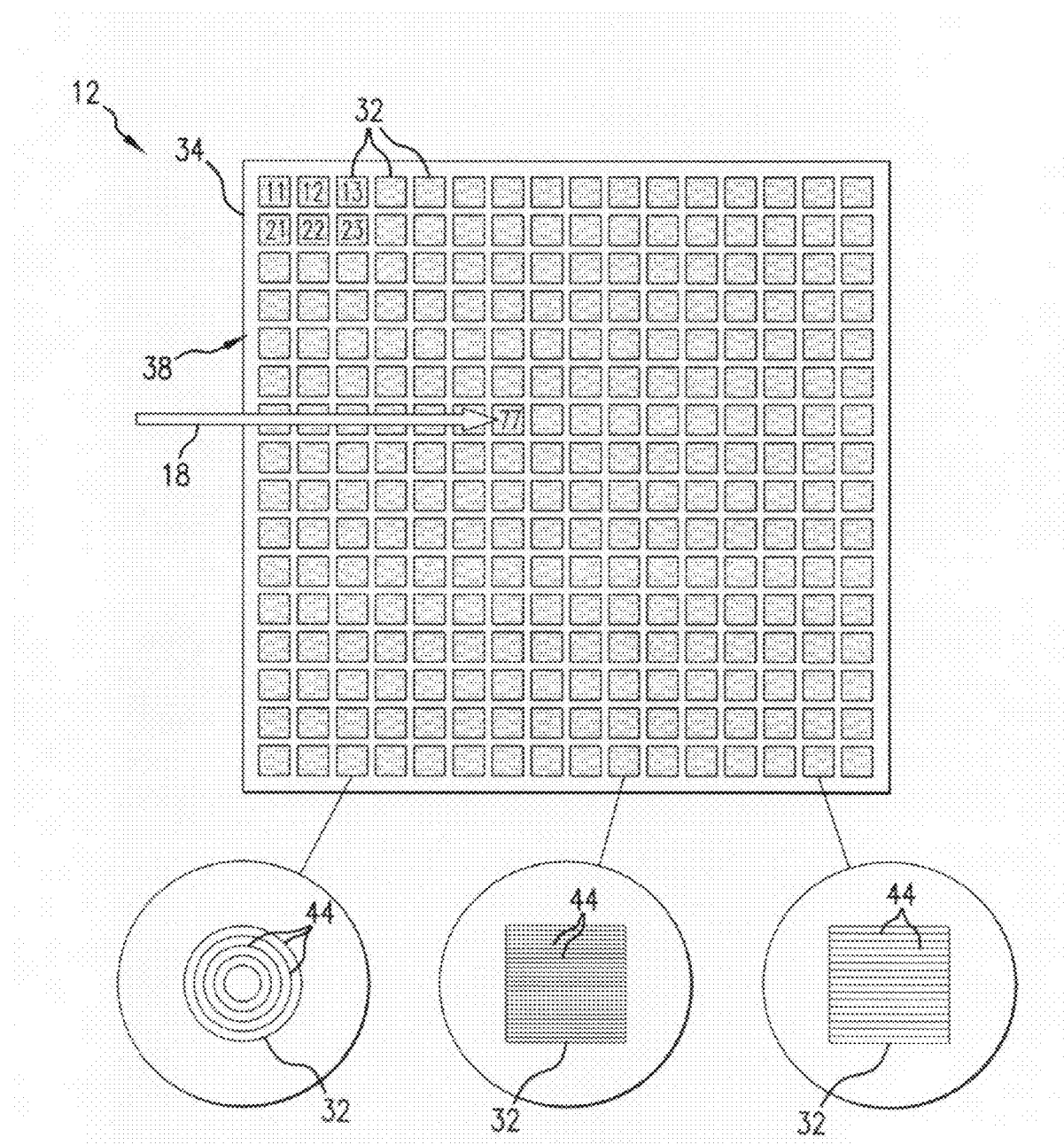
FIG. 4 is a schematic representation of the multi-patch sensor chip layout.

Referring to FIGS. 2A-2E and 4, the active sensor chip 12 may be configured in a single patch arrangement 32 or in a multi-patch chip arrangement 34, respectively. FIG. 4 schematically illustrates the multi-patch active sensor 34 where a plurality of single patches 32 are arranged in an array structure.

Referring again to FIGS. 2A-2E, each active sensor patch 32 includes a substrate 36 made of an optically transparent material, including glass, fused silica, sapphire, or a plastic. A metal film 38 is formed on the surface of the substrate 36. Preferably, the metal film 38 is made in the thickness range of 10-100 nm, with the preferred range in approximation of 50 nm. The metal film 38 may be formed of gold or silver.

The dielectric periodically patterned layer 40 is formed on the surface 42 of the metal film 38. The dielectric nano-structures may be made from any transparent material that may be processed photolithographically, by electron beam lithography or by ion beam lithography. For example the dielectric periodically patterned layer 40 may be made from polymethylmethacrylate (PMMA), lexan, silicon monoxide, silica, boron nitride, etc. As shown in FIGS. 2A-2E, the dielectric periodically patterned layer 40 includes a plurality of periodically disposed nano-elements 44 represented by undulations formed of walls 48 erected from the surface of the metal film 38 and trenches 50 are defined between the walls 48.

Figure 2A:
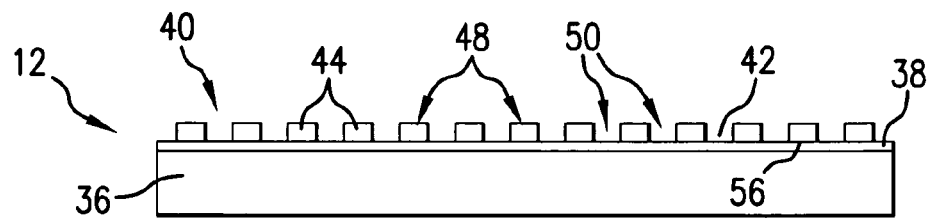
FIGS. 2A-2E represent alternative embodiments of the active sensor chip of the present invention.
Figure 2B:
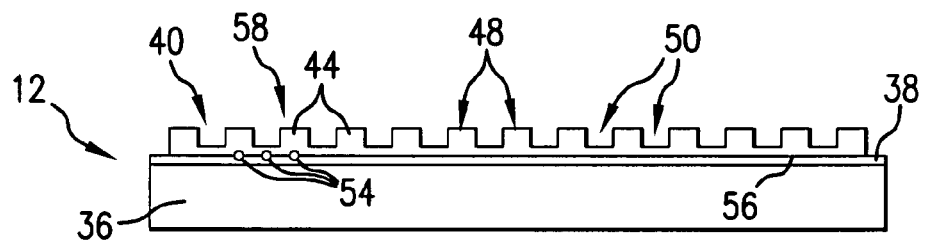
Figure 2C:
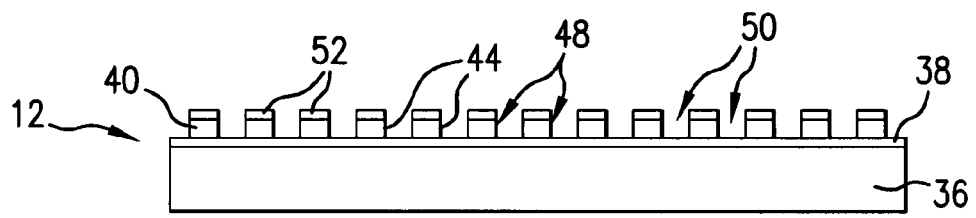
Figure 2D:
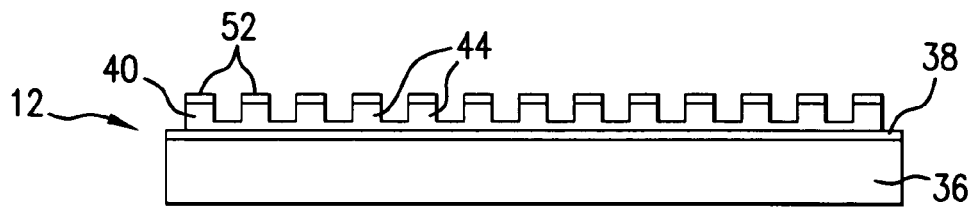
Figure 2E:
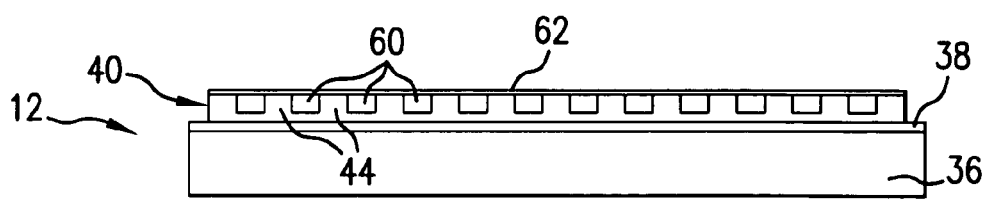

As shown in FIGS. 2A and 2C, the dielectric layer 40 may be etched between the walls 48 to the surface of the metal film 38, while, alternatively, as shown in FIGS. 2B and 2D-2E, there may be dielectric material remaining within the trenches 50.

Metal film 52 preferably formed from gold or silver, may be deposited on the top surface of the walls 48. The metal film 52 is a very thin gold layer with a thickness range of a few nm to allow surface attachment chemistry using the gold surface for surface functionalization, as will be described in detail in further paragraphs. The nano-structured dielectric layer 40 on the metal film 38 is used to provide a periodicity to allow momentum phase matching between the excitation light and surface plasmons (also referred to herein as Surfae-Plasmon Polaritons or plasmons) 54.

The dielectric periodically patterned patch 32, in a single patch implementation or in a multi-patch sensor implementation, is an active element in which the Surface-Plasmon Polaritons 54 are excited. Each patch 32 has a specific nano-structured periodicity and specifically shaped periodically disposed nano-elements 44. The surface plasmons 54 exist in a two dimensional domain defined by the boundary 56 between the metal film 38 and the dielectric periodically patterned layer 40. The Surface-Plasmon Polaritons are excited "from an", e.g. by illuminating the front surface 58 of the sensor patch 32 with control of the illumination vertical and azimuthal angles, polarization direction, as well as wavelengths of the incident excitation light beam for each patch periodicity. Once the Surface-Plasmon Polaritons 54 arc excited and start to propagate in the space in vicinity of the boundary 56, their trajectories are modified by the nano-elements 44 to produce excitation "hot spots", or patterns of excitation. By controlling the behavior of the Surface-Plasmon Polaritons, therefore, a control of the fluorescence patterns from surface hound fluorophores is possible in the present sensor system.

Shown in FIGS. 2A and 2B, the nano-structured dielectric layer 40 on the thin metal film 38 itself provides a periodicity to allow momentum phase matching between input light and the Surface-Plasmon-Polaritons 54. However, molecules attached to the metal film 38 in the trenches between dielectric walls 48 in a geometry shown in FIG. 2A could be inaccessible to binding because they are buried in a trench 50, or fluorophores could be quenched due to their proximity to the metal film 38. As shown in FIG. 2B, the surface of the metal film 38 is not exposed between the walls 48. In this design the fluorescent molecules are attached to the surface of the dielectric distant from the metal film that allows to avoid the quenching of their fluorescence into the air or surface liquid. Alternatively, as shown in FIGS. 2C and 2D, thin gold layer 52 is deposited on the top walls 48 which allows surface attachment chemistry using a metal surface for surface functionalization.

Shown in FIG. 2E, is a multi-layer patch structure in which two periodically patterned dielectric layers 40 and 60 are sandwiched between the metal film 38 and a metal film 62.

The nano-structured surfaces shown in FIGS. 2A-2E represent several alternative geometry designs used to provide phase matching so that plasmons may be efficiently excited from air with controlled illumination. However, it is to be understood, that other design arrangements for the active sensor chips 12 are also contemplated in the present sensor system 10. For example, a multi-layer arrangement including a plurality of metal films with the plurality of dielectrical periodically patterned layers intermittently stacked with the metal films may constitute alternative embodiment of the sensor of the present invention.

Figure 3:
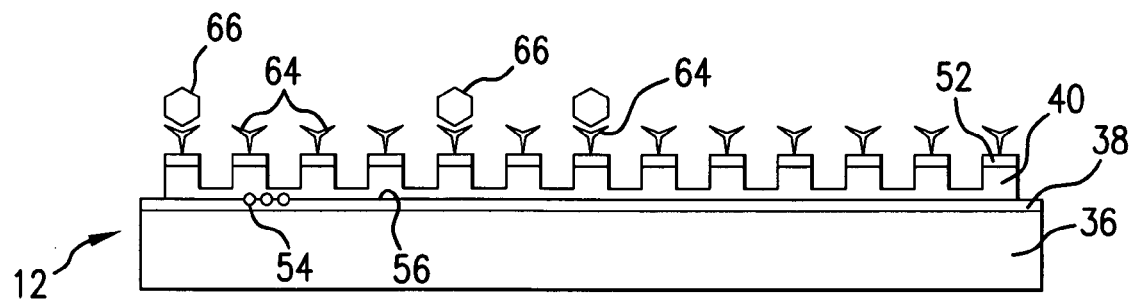
FIG. 3 is a schematic representation of the periodically patterned dielectric patch with the functionalized surface.

An important application of the nano-structured Surface-Plasmon Polariton fluorescent sensor of the present invention is for biological or chemical sensing where the surface of the dielectric periodically patterned layer 40 is "functionalized" with surface tags 64 that bind specifically to fluorescent target molecules (or other particles) 66, such as for example DNA, oligonucleotides, C-DNA, RNA, antibodies, antigens, proteins, cells, etc. as shown in FIG. 3. The surface tags 64 are attached in locations that place them in the evanescent field of the Surface-Plasmon Polaritons 54 localized at the metal-dielectric boundary 56. The evanescent fields extend above the metal film 38 a distance on the order of a wavelength of the excitation light 18.

In the multi-patch sensor arrangement 34 best shown in FIG. 4, individual patches 32 may be dimensioned on a scale from tens of μm to millimeters. The entire multi-patch sensor chip 34 may have size in ranges from millimeters to centimeters.

Different patches 32 of the multi-patch sensor chip 34 may be contoured in different configurations such as for example in square, circular, elliptical or rectangular shapes. The patches 32 on the ship 34 also may differ in periodicity, different spacings as well as shapes of nano-elements 44. For example, the shapes of the nano-elements 44 may include parallel lines with different spacing, concentric circles with different spacing, parabolas, ellipses. The periodically disposed nano-elements 44 may also be presented as arrays of shapes in a matrix arrangement such as holes, bumps, repeated shapes of different symmetry, and generally any shape which is applicable in plasmonics and can be formed in repeated pattern on the surface of the metal film.

In the arrangement of the present invention, the fluorescence pattern as well as the strength of the fluorescence response from the target particle 66 of the space specimen 28 may be controlled by controlling the behavior of the Surface-Plasmon Polaritons 54. This control is carried out by the processor unit 23 through the controller unit 24 operatively coupled to the source of excitation light 16 as well as to the stage 14. The controller 24 controls the wavelength of the excitation light beam 18, as well as a relative disposition thereof, and its polarization orientation with regard to the nano-elements 44 of the active sensor patch 32.

The processor unit 23 performs the necessary calculations in the system 10 and applies control parameters through the controller 24 to the laser 16 and/or the stage 14 to control PPS behavior in the active sensor chip 12 in order to provide optimal conditions for obtaining the strongest fluorescence response at each patch 32 depending on the periodicity and/or geometry of the periodically-patterned nano-structured dielectric layer 40. For this purpose, in the chip interrogation process, the processor 23 requests a periodicity and/or geometry of the illuminated patch 32 under study (or scheduled for study at a predetermined time) from a database 19 residing in the memory 29 of the computer 17 or on a separate carrier. The database 19 contains addresses of the patches 32 on the multi-patch sensor chip 34 and associated therewith periodicities and geometries of the dielectric nano-structures. Once this data is available, the processor consults with the database 25 for the control parameters, e.g., wavelength, incidence angle, azimuth angle, and polarization orientation optimal for the periodicity and/or geometry of the current patch. The database 25 also may contain the relationships between the optimal control parameters and the type of the fluorescent dye used at the current patch under study.

Upon obtaining the optimal control parameters, the processor 23 communicates the same to the controller unit 24, which further issues corresponding commands to the laser 16 and the optics associated therewith and/or to the stage 14 to attain the optical conditions in the system for generation of the strongest fluorescent response in the current patch.

The processor 23, controller 24, and the memory 29 may reside on the same computer 17, or alternatively, these elements may constitute independent units communicating each with the other for the purposes and objectives presented in the previous paragraphs.

As shown in FIGS. 1 and 4-7, the control unit provides two modes of interrogation, e.g., (a) the mode where the patches 32 on the multi-patch chip 34 are illuminated with the light beam, such as for example, laser light 18, in a predetermined sequential order, or (b) the mode in which a selected patch is illuminated one at a time. For example when different specimens 28 are positioned on different active sensor patches 32 in the chip 34, it may be desirable to interrogate chips 32 one after another for instance in "row after row" order, or "column after column" sequence, etc. Alternatively, individual patches of interest may be illuminated, as for example shown in FIG. 4 where only the patch 77 with the specimen of interest is illuminated for the specimen analysis.

Figure 5:
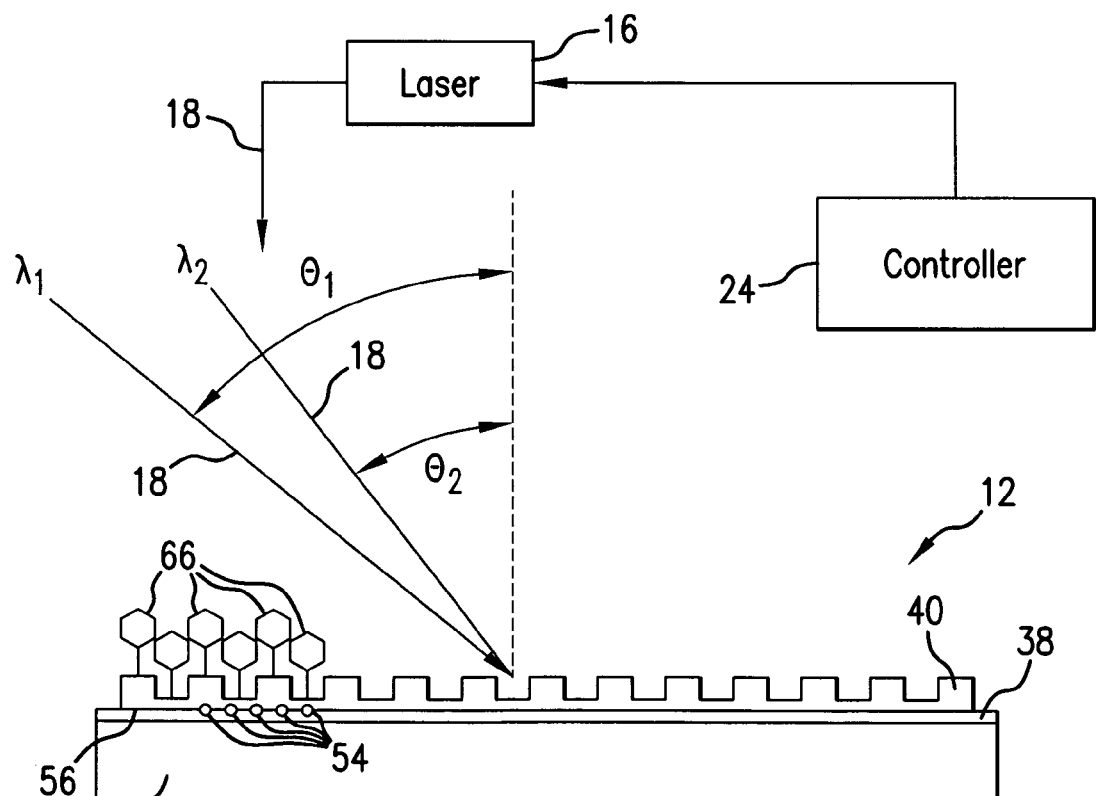
FIG. 5 is a schematic representation of the dielectric periodically patterned sensor patch illuminated by the light with controlled distinct wavelengths ($\lambda_1$, $\lambda_2$) and at different incidence angles ($\theta_1$, $\theta_2$)

When the patches on the chip 34 are illuminated in the predetermined sequential order, as provided by the control unit 24, due to the fact that each patch 32 may be characterized by different periodicity, different shapes of nano-elements 44, and due to the fact that the specimen 28 on different patches 32 may be fluorescently labeled by different surface tags, in order to provide the optimal conditions for strong fluorescent response from each patch 32, the control unit 24 changes the wavelength $\lambda$ of the excitation light beam 18 when moving from one patch 32 to another as well as controls the incidence angle $\theta$ of the excitation light beam on each patch 32 as a function of the periodicity of the illuminated patch 32, as shown in FIG. 5.

Figure 6:
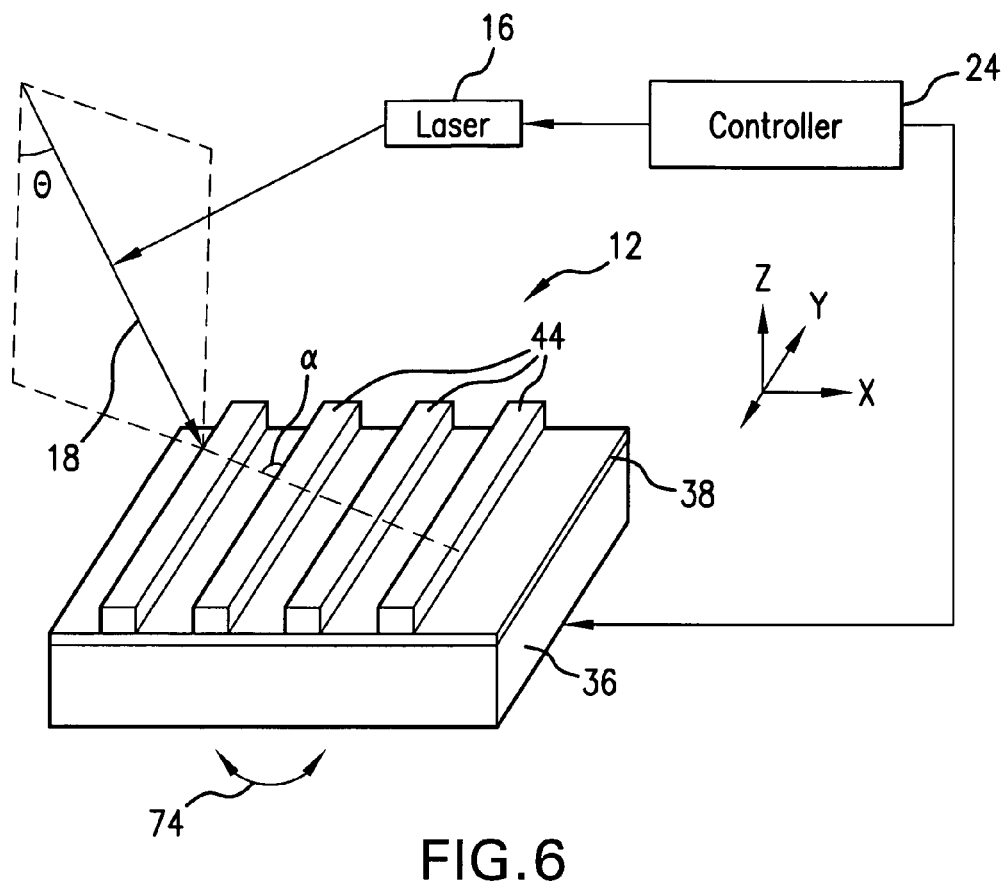
FIG. 6 is a schematic representation of controlling principles involving variation of the azimuthal orientation of the excitation light beam relative to the periodically disposed nano-elements on the patch.

Control unit 24 also controls the azimuthal orientation of the excitation light beam relative to the nano-elements 44 as shown in FIG. 6 where the controller either controls the direction of the laser beam 18 through a system of directing mirrors (not shown) or by rotating the stage 14 relative to the stable laser beam by actuating a motor 70 for the rotational displacement to the stage 14 in a direction and at an angle based on calculations provided by the processor 23 to the controller 24.

Figure 7:
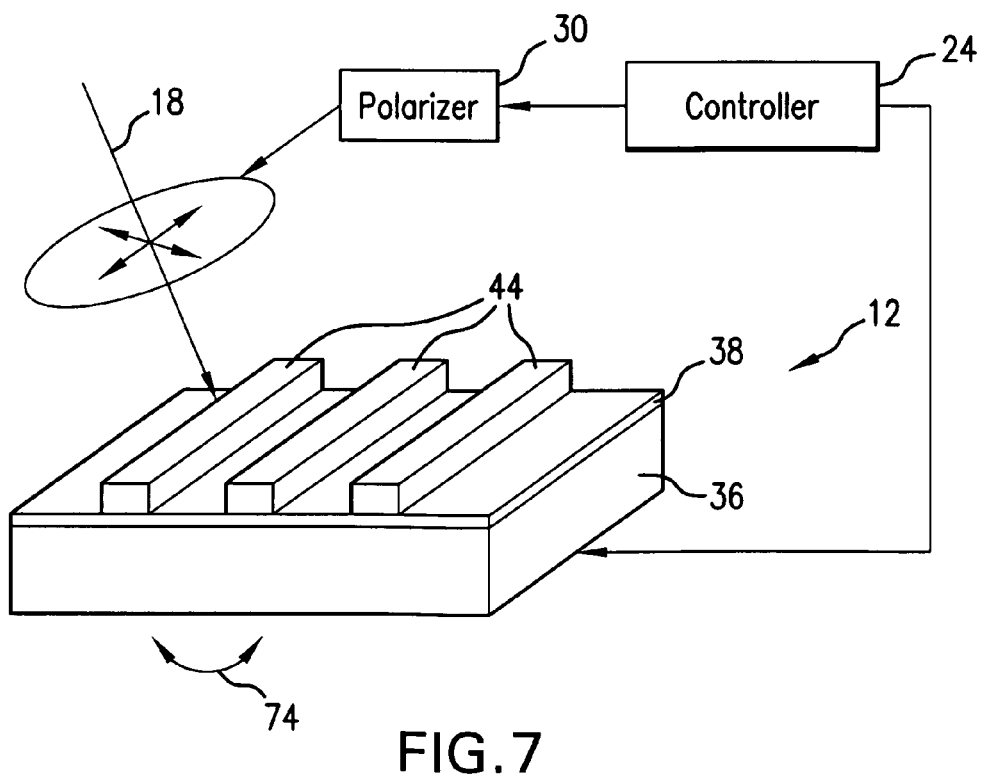
FIG. 7 is a schematic representation of the controlling principles involving alteration of polarization direction of the excitation light beam relative to the periodically disposed nano-elements on the patch.

The polarization direction of the excitation light beam relative to the nano-elements 44 is controlled, as shown in FIG. 7, by controlling the polarizer 30. All of these parameters are controlled for the efficient plasmon excitation and the resultant strong fluorescence intensity for each patch 32 depending on the periodicity and the shape of the nano-elements 44 of each patch 32. The processor 23 provides the controller 24 with control parameters read from the database 25 for the periodicity and/or geometry of the illuminated patch 32.

In one embodiment, the sensor system 10 contemplates a change of the direction of the incident laser beam with the system of mirror and lens arranged in a predetermined order so that the incidence angle $\theta$ may be changed by changing the direction of the laser beam 18 relative to the patch 32. In another embodiment the controller unit 24 actuates the stage 14 through a system of motors 70 to translate the stage 14 with the active sensor chip 12 attached thereto in xy directions below a localized laser illumination spot which illuminates one patch of the multi-patch sensor chip 34 at a time. Alternatively, in order to change the azimuth angle $\alpha$, the controller unit 24 actuates the stage 14 for bidirectional rotation as shown by the arrow 74 to change the relative disposition between the laser beam 18 and the nano-elements 44.

The operational principles, design and underlying software of the controller unit 24 and processor 23, as well as specifics of the linear and rotational action actuator 70, in addition to design specifics of the polarizer 30 do not constitute the inventive concept of the present sensor system 10, and therefore are not presented herein in detail.

The sensor system of the present invention is perfectly compatible with the detector unit in the form of the fluorescence microscope 76 equipped with the image acquisition unit 21, which may include a digital camera, CCD, CMOS, or IR camera which communicates the images to the processor unit 23 for further processing and analysis. The acquired images are compared with data in the reference database 26. As the result, the processor 23 generates a signal indicating the nature of the particle of interest found in the specimen.

Figure 8:
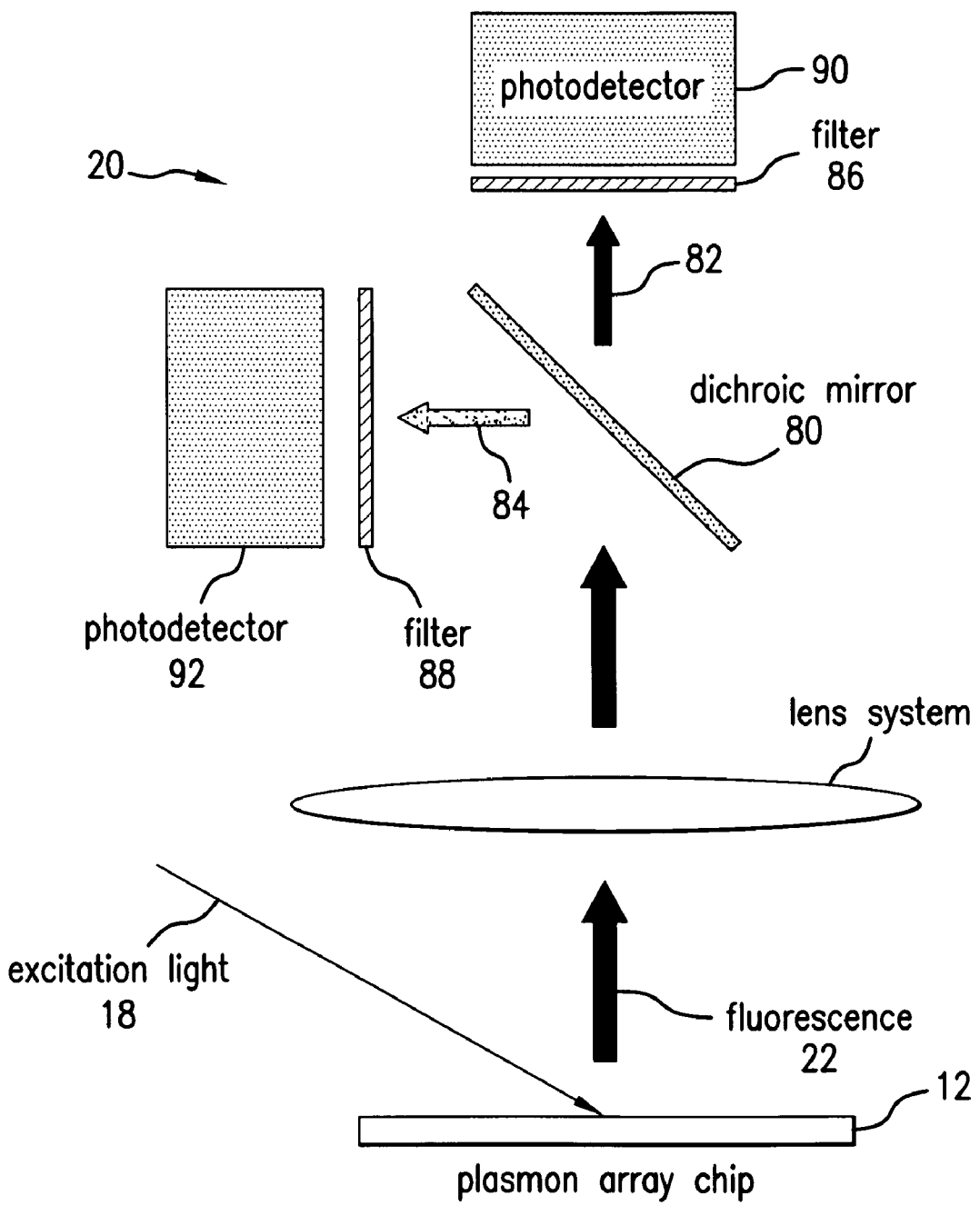
FIG. 8 is a schematic representation of the detector using an optional dichroic mirror to allow the simultaneous detection of fluorescence at two separate wavelengths on different patches of the chip.

Shown in FIG. 8 is a dichroic mirror 80 used optionally in the detector scheme if the fluorescence signal is obtained from the multi-patch chip 34 by the simultaneous detection of fluorescence at two separate wavelengths which may result from different fluorophores on different patches 32 of the chip 34. In this arrangement, the dichroic mirror 80 splits the fluorescence response into two signals 82 and 84 which are further filtered by filters 86 and 88. The filters pass a fluorescence signal portion corresponding to a respective one of the two wavelengths to the photodetectors 90 and 92 for detection and further processing in the computer 17. In another embodiment more than two wavelengths of fluorescence may be detected simultaneously using combinations of dichroic mirrors and filters.

Experiments have been conducted for understanding of the mechanism of how the patterned dielectric structure affects the behavior of the SPPs.

Comparison Between a Grating Deposited onto a Metal Layer and an Evanescent Grating Coupler A layer of fluorescent material (R6G) dissolved in ethanol has been spin-coated onto a PMMA grating structure. 40 nm thick PMMA nano-stripe gratings have been formed by E-beam lithography on the top of two kinds of substrates: an ITO/Glass and an Au/Glass substrates. The thickness of the Au layer was about 50 nm. A typical periodicity of the PMMA stripe gratings shown in FIG. 9C was 500 nm.

Figure 9A:
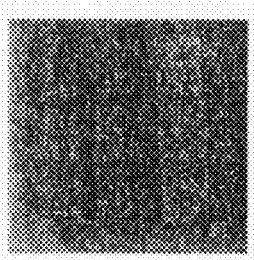
FIGS. 9A-9B represent the pictures of fluorescence emission for R6G/PMMA gratings on ITO/glass substrate (FIG. 9A) and for an Au/glass substrate (FIG. 9B)
Figure 9B:
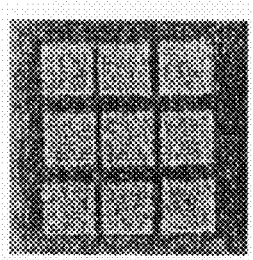
Figure 9C:
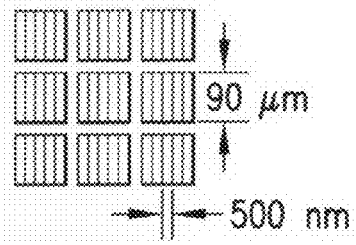
FIG. 9C shows the arrangement of gratings on the surface of the samples.

All samples have been examined under a fluorescence optical microscope. The wavelength of the excitation filter was centered at 560 nm with 40 nm bandwidth. The emission barrier filter was located at 610 nm. The emission peak of R6G (in ethanol) was 590 nm. The fluorescence images are shown in FIGS. 9A, 9B, wherein FIG. 9A corresponds to R6G on ITO substrates, and FIG. 9B corresponds to R6G on Au film substrates. The sample surfaces were prepared using the same procedure, and the images were taken with identical exposure times and gains of the CCD camera used in the fluorescence microscope.

In order to analyze the obtained data numerically, the digital values of the signal for each pixel of the JPEG image file produced by the CCD camera were extracted and the ratios of the digital values (DV) at different pixels were compared. These ratios were analyzed by taking into account the gain factor $\Gamma$ of the CCD camera. Typical values of $\Gamma$ range from 0.45 to 2.5, and the light intensity is related to the digital value (DV) according to Intensity=const(DV)$^\Gamma$. The CCD of the fluorescence microscope used in the experiments was set at $\Gamma \sim 2.2$ in order to emulate the response of the human eye. As can be seen from FIGS. 9A and 9B, the fluorescence of R6G deposited on top of the unperturbed PMMA layer (without a grating) is barely detectable, while the fluorescence coming from the PMMA gratings formed on top of the gold film is the brightest. Compared to the grating on the ITO substrate the fluorescence is enhanced by at least a factor of 10. In this example, the grating pitch and the excitation polarization were not optimized. Since fluorescence microscopes (FOM) are commonly used in bio-detection, it is concluded that these results indicate the competitive potential of the geometry of the present sensor in biosensing applications.

Polarization and Periodicity Dependence

Figure 10A:
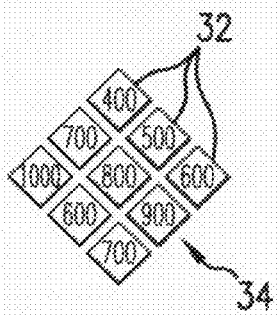
FIGS. 10A-10C represent the results of a fluorescence study dependent on polarization and periodicity.
Figure 10B:
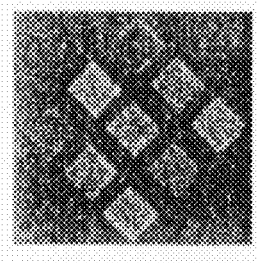
Figure 10C:
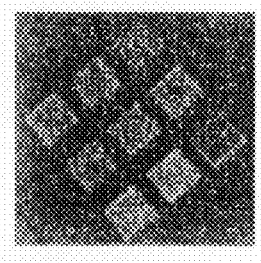

In order to understand how the fluorescence signal taken with the FOM is affected by the periodicity of the gratings, a sample was prepared with regions of different periodicity varying from 400 nm to 1 μm. The sample geometry is illustrated in FIG. 10A, in which the grating periodicity is given in nanometers. FIGS. 10B-10C indicate that the fluorescence enhancement depends strongly on the grating periodicity.

Figure 11:
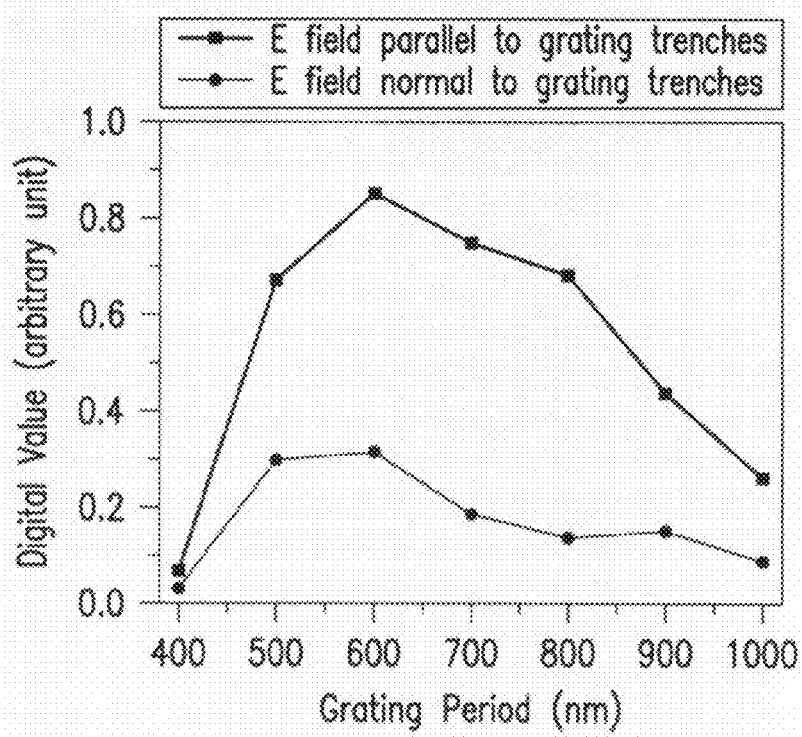
FIG. 11 is a diagram representing a polarization effect on gratings with normal incidence to the sample surface.

The polarization dependence of the observed effect was also studied. In this experiment a mercury lamp filtered by a film polarizer was used as the excitation source at normal incidence. The sample was rotated so that the polarization direction was changed with respect to the grating trenches. The results of these experiments are shown in FIGS. 10B, 10C and 11. The exposure time for FIGS. 10B and 10C was 250 s and 700 s respectively. FIG. 11 shows the normalized digital value taken from the images presented in FIGS. 10B-10C. Every value was normalized to the background and the exposure time. The fluorescent efficiency was 10 times higher when the E field was parallel to the grating trenches.

It is suggested that some kind of surface Plasmon polariton excitation is involved in the phenomena observed in the experiments. If the SP dispersion is computed and the k-momentum is matched thereto, it is found that for 640 nm emission, the plasmon mode and radiation mode are strongly coupled because of k-vector momentum matching provided by the grating and the emission angle is zero degree when the grating periodicity is 736 nm.

In order to study the enhancement mechanism in more detail it was studied how the excitation angle affects the fluorescence excited at various grating periodicities.

Rotation of Incident Angle

Figure 13:
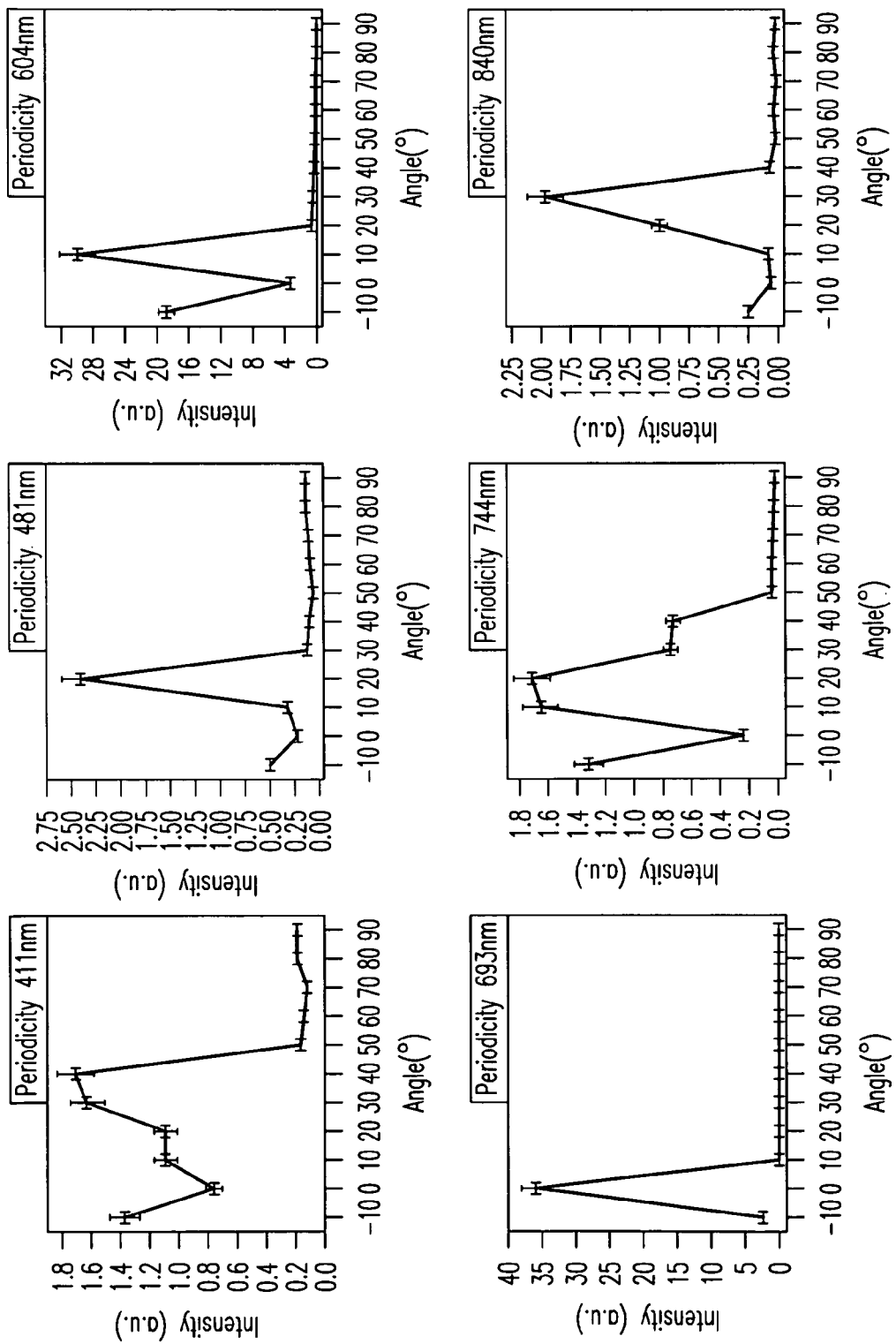
FIG. 13 are diagrams representing fluorescence emission versus incidence angle for different periodicities of the periodically patterned active sensor patches.

A one-dimensional (1D) PMMA grating on an Au film surface acts like a 1D plasmonic crystal. In order to relate the fluorescence enhancement with plasmonic crystal properties of the substrates in the prepared samples, more detailed measurements of fluorescence at different angles of the excitation light were performed. In these experiments the incident laser light was tilted at an angle θ with respect to the z-axis and rotated by an angle α with respect to the y-axis in the x-y plane as shown in FIG. 6. The emission intensity of each pattern is recorded with the α rotation of every 10 degrees. FIGS. 12A-12C show two patterns illuminated at different rotation angles α. In FIG. 12A, 411 nm and 840 nm patterns emit efficiently, while in FIG. 12B, the most efficient fluorescence is obtained from the 693 nm pattern. FIG. 12C indicates the position and periodicity of different gratings. The fluorescence signal measured as a function of angle is shown in FIG. 13 for different periodicities of the PMMA gratings. The background signal was subtracted from every data point and normalized to the CCD exposure time. The angle α is scanned from −10 to 90 degrees.

Figure 14:
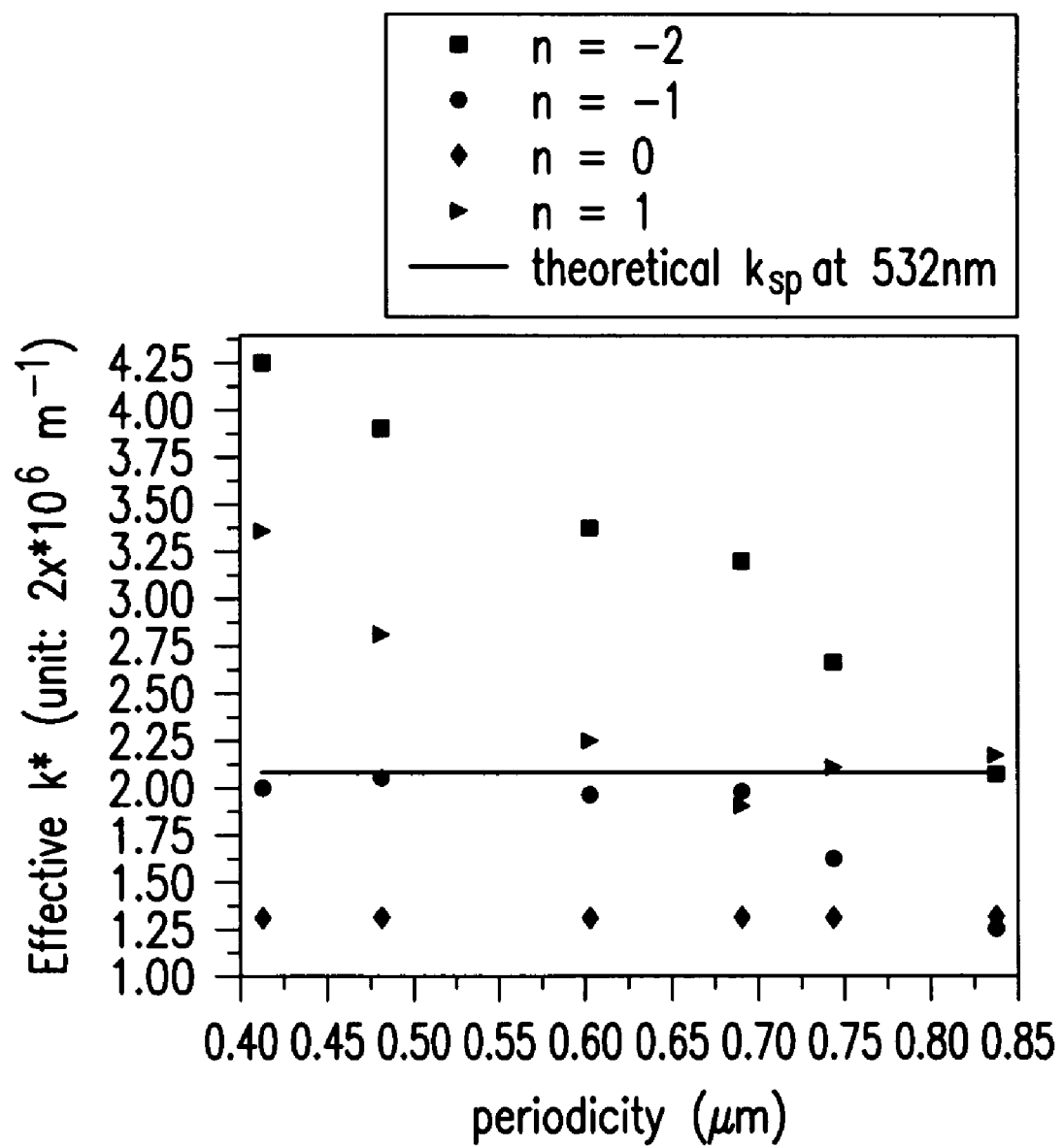
FIG. 14 is a diagram showing the relationship of the incident wave vector k, periodicity and fluorescent intensity.

The angle α, which corresponds to the maximum of the fluorescence signal, can be determined from FIG. 11. The error of the measured angle is in a range of ±2.5°. The reason for the unsymmetrical intensity at −10° and +10° is that α is not accurately tuned to a symmetrical position. To explain the angle effect, the incident wave vector $k_o=2\pi/532$ nm is decomposed as the projected wave vector $k_o \sin\theta$ in the x-y plane and $k_o \cos\theta$ along the z-axis. The component $k_o \cos\theta$ can be decomposed into x and y components as $k_o \sin\theta \sin\alpha$ and $k_o \sin\theta \cos\alpha$, respectively. The grating k vector $2\pi n/a$ can provide momentum matching along the x direction as shown in eq. (1), while the y component remains unchanged as shown in eq. (2). If a surface plasmon is excited, the k-vector of the incoming photons mediated by the grating periodicity should match the k vector of surface plasmons as shown in eq. (3).

$$k_x^* = k_o \sin\theta \sin\alpha + (2\pi n/a) = k_{sp}^\perp \quad (1)$$

$$k_y^* = k_o \sin\theta \cos\alpha = k_{sp}^\parallel \quad (2)$$

$$(k^*)^2 = (k_o \sin\theta \cos\alpha)^2 + (k_o \sin\theta \sin\alpha + \pi n/a)^2 = (k_{sp})^2 \quad (3)$$

where n is an integer k* for n=2, −1, 0, and 1. FIG. 14 shows k* for n=2, −1, 0, and 1. At least one good integer order n can be fitted to the theoretical $k_{sp}$ for every periodicity.

Table 1 shows the coupling order n, the maximum excitation angle α and the maximum digital value of the image intensity for each periodicity. The digital values for each period are comparable to each other because they are normalized to the exposure time. For 604 nm and 693 nm, the coupling order is ±1, which shows a higher fluorescence intensity compared to other gratings for which only one diffraction order is coupled efficiently.

TABLE 1

|  | Periodicity (nm) | | | | | |
|---|---|---|---|---|---|---|
|  | 411 | 481 | 604 | 693 | 744 | 840 |
| α (degrees, max fluorescence) | 35 | 20 | 8 | −2 | 15 | 30 |
| Order n | −1 | −1 | −1, +1 | −1, +1 | 1 | −2, +1 |
| Max intensity (a,u,) | 1.7 | 2.4 | 29.8 | 36.0 | 1.7 | 2.0 |

The active sensor chip 12 may be illuminated from the front (air) or back sides thereof. It is especially advantageous to excite the SPPs with pumping light delivered from the front side of the sample, which is compatible with the geometry of current commercial fluorescence optical microscopes (FOM). If a laser is incident from the front at a certain angle θ, the sample may be rotated horizontally under the FOM 76 and the effective periodicity in the patch is changed by the rotation.

The corrugated surface structure can help to capture more test material, which increases the concentration of fluorophore labels near the surface. In addition, the corrugated surface structures can hold binding agents and/or fluorophores in close proximity to the metal film, which is the place where fluorescence by SPPs is efficiently excited. Thus the structure discriminates against fluorescence from non-bound fluorophores in a specimen above the surface. The evanescent field of the plasmons only extends away from the metal surface by about one wavelength, so free-floating moieties that are above the surface, but are not attached are highly unlikely to be excited and to fluoresce.

Further, in genomic and proteomics applications, an array of periodic structures with different periodicities allows multi-dimensional variation of fluorescent gene chip patterns. Not only is the fluorescence from each chip element a function of selective binding of fluorescently labeled oligonucleotides antigens or antibodies, the spatial location on the chip can determine the wavelength at which fluorophores are excited and the wavelengths of different fluorophores themselves. This allows clearer differences in spatial/color/excitation wavelength patterns for more positive binding pattern evaluation.

Although this invention has been described in connection with specific forms and embodiments thereof, it will be appreciated that various modifications other than those discussed above may be resorted to without departing from the spirit or scope of the invention as defined in the appended claims. For example, equivalent elements may be substituted for those specifically shown and described, certain features may be used independently of other features, and in certain cases, particular applications of elements may be reversed or interposed, all without departing from the spirit or scope of the invention as defined in the appended claims.

What is claimed is:

1. Sensor system with Surface-Plasmon-Polariton (SPP) enhanced selective fluorescence excitation, comprising:
   a. an active sensor chip including:
      at least one conductive layer formed from a conductive material,
      at least one dielectric layer formed from a dielectric material and deposited on a first surface of said at least one conductive layer, surface plasmon polariton existing in vicinity of a boundary between said at least one conductive layer and said at least one dielectric layer, said at least one dielectric layer being patterned to form at least a first active sensor patch having a periodically-patterned surface of a predetermined first periodicity formed of a plurality of periodically disposed nano-elements, wherein said periodical-patterned surface includes dielectric undulations forming walls having spaced apart steep sides extending from above said first surface of said at least one conductive layer, and trenches defined between said walls, and wherein said steep sides of said walls are devoid of a conductive material,
      at least a first specimen under study being positioned above said periodically patterned surface of said at least first active sensor patch, said at least first specimen containing at least first fluorescently labeled target particles of interest; and
   b. a multi-planar adjustable source of excitation generating an excitation light beam of at least a first wavelength, said excitation light beam being incident on said periodically patterned surface of said at least first active sensor patch through said at least first specimen under study at a first adjustable polar incidence angle and at a first adjustable azimuthal orientation relative to said nano-elements;
   wherein said at least first target particles of interest generate a first fluorescence signal enhanced by controlling the excitation of said surface plasmon polaritons in vicinity of said boundary through selecting an optimal at least one of said first wavelength, said first incidence angle, and said first azimuthal orientation for said first periodicity.

2. The sensor system of claim 1, wherein said active sensor chip further includes at least a second active sensor patch having a second periodically-patterned surface of a predetermined second periodicity and positioned at a predetermined location relative to said at least first active sensor patch on said at least one conductive layer.

3. The sensor system of claim 2, wherein at least a second specimen under study containing at least second fluorescently labeled target particles of interest is positioned above said second periodically-patterned surface of said at least second active sensor patch, said at least second fluorescently labeled target particles of interest generating a second fluorescence signal.

4. The sensor system of claim 3, further comprising a processor unit operatively coupled to said source of excitation and controlling interrogation of said active sensor chip in a predetermined interrogation mode, said predetermined interrogation mode being selected from a group consisting of:
   illumination of said at least first and second active sensor patches with said excitation light beam in a predetermined sequential order, illumination of said at least first active sensor patch, and illumination of said at least second active sensor patch.

5. The sensor system of claim 4, wherein said processor unit controls said at least first wavelength of said excitation light beam in accordance with said first periodicity and said second periodicity of said periodically-patterned surfaces of said at least first and second active sensor patches, respectively, to control said first and second fluorescence signals generated by said at least first and second target particles of interest, respectively.

6. The sensor system of claim 4, wherein said processor unit controls said first incidence angle and said first azimuthal orientation of said excitation light beam relative to said nano-elements of said at least first and second active sensor patches, respectively, in accordance with said first and second periodicities thereof to control said first and second fluorescence signals generated by said at least first and second target particles of interest, respectively.

7. The sensor system of claim 4, wherein said processor unit is further operatively coupled to said active sensor chip to control a linear and rotational displacement thereof relative to said incident excitation light beam.

8. The sensor system of claim 3, further comprising a detector unit positioned in a direct optical contact with said active sensor chip through said at least first specimen under study.

9. The sensor system of claim 8, wherein said detector unit includes a fluorescent microscope.

10. The sensor system of claim 8, wherein said detector unit includes a dichroic mirror for separating said at least first and second fluorescence signals, at least a first and second photodetector, each for detection of a respective one of said at least first and second fluorescence signals.

11. The sensor system of claim 2, wherein each of said at least first and second active sensor patches is contoured in a predetermined shape.

12. The sensor system of claim 1, wherein said periodically disposed nano-elements of said at least first active sensor patch are shaped in a predetermined geometry.

13. The sensor system of claim 1, further comprising a conductive film covering top portions of said walls of said periodically-patterned surface, said top portions extending between said spaced apart steep sides of said walls.

14. The sensor system of claim 1, further comprising at least another conductive layer, said at least one periodically-patterned surface layer being sandwiched between said at least one and said at least another conductive layers.

15. The sensor system of claim 14, further comprising at least another periodically patterned dielectric laser formed in contact with said periodically-patterned surface of said at least one dielectric layer thereby creating a multi-dielectric periodically patterned structure, said multi-dielectric periodically patterned structure being sandwiched between said at least one and said at least another conductive layers.

16. The sensor system of claim 1, further comprising a plurality of conductive layers and a plurality of periodically nano-structured dielectric layers intermittently stacked to form a multilayered said at least first active sensing chip.

17. The sensor system of claim 1, wherein said periodically patterned surface provides momentum phase matching between said incident excitation light beam and said excited surface plasmon polaritons.

18. The sensor system of claim 1, further comprising a polarizer optically coupled between said source of excitation and said active sensor chip, said polarizer polarizing said incident excitation polarization light beam in a predetermined polarization direction relative to said periodically disposed nano-elements.

19. The sensor system of claim 1, wherein said source of excitation includes a laser.

20. The sensor of claim 1, wherein said source of excitation is a multi-wavelength source of excitation.

21. A method for enhancing selective fluorescence excitation in a sensor system, comprising the steps of:
forming at least first periodically-patterned dielectric patch of a first periodicity on a conductive layer, said at least first periodically patterned dielectric patch including a plurality of periodically disposed nano-elements, wherein said periodically-patterned dielectric patch includes dielectric undulations forming walls having spaced apart steep sides extending from above a surface of said conductive layer, and trenches defined between said walls, and wherein said steep sides of said walls are devoid of a conductive material, functionalizing said at least first periodically patterned dielectric patch with first surface tags,
positioning at least a first specimen under study above said at least first periodically patterned dielectric patch, said at least first specimen under study containing at least first fluorescently labeled target particles bound to said first surface tags,
exciting surface plasmon polaritons in vicinity of a boundary formed between said at east first periodically patterned dielectric patch and said conductive layer by applying an excitation light beam from a multi-planar adjustable source of a first wavelength onto said at least first periodically patterned dielectric patch through said at least first specimen at a first adjustable polar incidence angle and at a first azimuthal orientation relative to said nano-elements, a fluorescence signal being generated by said at least first fluorescently labeled target particles depending on behavior of said excited surface plasmon polaritons, and
controlling said surface plasmon polaritons behavior to enhance said fluorescence signal by selecting an optimal at least one of said first wavelength, said first incidence angle, and said first azimuthal orientation for said first periodicity.

22. The method of claim 21, further comprising the steps of selecting said first surface tags in accordance with said first periodicity.

23. The method of claim 21, further comprising the steps of:
polarizing said excitation light beam at a polarization angle relative to said periodically disposed nano-elements selected in accordance with said first periodicity.

24. A method for detecting fluorescence in specimens, comprising the steps of:
forming a multi-patch sensor chip including a plurality of periodically patterned dielectric active sensor patches on a conductive layer, each of said plurality of active sensor patches including a plurality of periodically disposed nano-elements wherein each said periodically patterned dielectric active sensor patch includes dielectric undulations forming walls having spaced apart steep sides extending from above said first surface of said at least one conductive layer, and trenches defined between said walls, and wherein said steep sides of said walls are devoid of a conductive material, functionalizing said each periodically patterned dielectric active sensor patch with a respective surface tag,
providing a plurality of specimens, positioning each of said plurality of the specimens on a respective one of said plurality of periodically patterned dielectric sensor patches functionalized by said respective surface tag,
illuminating said plurality of periodically patterned dielectric active sensor patches by an excitation light beam through said respective specimens positioned thereon in a predetermined sequential order, thereby causing generation of a respective fluorescence response from respective fluorescently labeled target particles of interest in said respective specimen, said fluorescence response being assisted by surface plasmon polaritons excitation in vicinity of a boundary formed between said conductive layer and said respective periodically patterned dielectric active sensor patch,
controlling a parameter selected from a group consisting of:
wavelength of said excitation light beam, incidence angle of said excitation light beam relative to said respective active sensor patch, azimuthal orientation of said excitation light beam relative to said periodically disposed nano-elements, and polarization angle of said excitation light beams relative to said periodically disposed nano-elements,
optimizing said parameter according to said periodicity or said illuminated respective periodically patterned dielectric active sensor patch, and
detecting said respective fluorescence response.

25. The method of claim 24, further comprising the step of scanning said excitation light beam over said plurality of periodically patterned active sensor particles of said multi-patch sensor chip.

26. The method of claim 24, further comprising the step of controlling a linear displacement of said multi-patch sensor chip relative to said excitation light beam.

27. The method of claim 24, further comprising the step of controlling an angular displacement of said multi-patch sensor chip relative to said excitation light beam to control said azimuth orientation thereof.

* * * * *